United States Patent
Liu

(10) Patent No.: US 11,348,290 B2
(45) Date of Patent: May 31, 2022

(54) SYSTEMS AND METHODS FOR IMAGE CORRECTION

(71) Applicant: SHANGHAI UNITED IMAGING HEALTHCARE CO., LTD., Shanghai (CN)

(72) Inventor: Yanyan Liu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 128 days.

(21) Appl. No.: 16/929,176

(22) Filed: Jul. 15, 2020

(65) Prior Publication Data

US 2020/0342638 A1     Oct. 29, 2020

(30) Foreign Application Priority Data

Jul. 15, 2019 (CN) .......................... 201910635815.X

(51) Int. Cl.
*G06T 11/00* (2006.01)
*A61B 6/03* (2006.01)

(52) U.S. Cl.
CPC ............ *G06T 11/005* (2013.01); *A61B 6/032* (2013.01); *G06T 2207/10081* (2013.01)

(58) Field of Classification Search
CPC ......... G06T 11/005; G06T 2207/10081; G06T 3/4007; G06T 11/008; A61B 6/032; A61B 6/5217; A61B 6/5258
See application file for complete search history.

(56) References Cited

U.S. PATENT DOCUMENTS

2009/0046833 A1* 2/2009 Hirokawa .............. A61B 6/542
378/108
2019/0378248 A1* 12/2019 Ida ......................... G01S 7/4808

* cited by examiner

*Primary Examiner* — David P Porta
*Assistant Examiner* — Mamadou Faye
(74) *Attorney, Agent, or Firm* — Metis IP LLC

(57) ABSTRACT

The present disclosure provides a system and method for image correction. The method may include obtaining image data of a target object; determining a target image based on the image data; determining a target aspect ratio of the target object in the target image; determining a correction function for correcting artifacts in the target image based on the target aspect ratio; and obtaining a corrected image of the target image by correcting the target image based on the correction function.

20 Claims, 8 Drawing Sheets

1100

Obtaining a reference set including a plurality of reference pairs, each reference pair of the plurality of reference pairs corresponding to a reference aspect ratio and a reference function with respect to the reference aspect ratio ~ 1110

Determining the correction function based on the reference set and the target aspect ratio ~ 1120

SYSTEMS AND METHODS FOR IMAGE CORRECTION

CROSS-REFERENCE TO RELATED APPLICATIONS

This application claims priority to Chinese Patent Application No. 201910635815.X, filed on Jul. 15, 2019, the contents of which are hereby incorporated by reference.

TECHNICAL FIELD

The present disclosure relates to image processing, and more particularly relates to systems and methods for image correction.

BACKGROUND

A medical imaging device (e.g., an electronic computed tomography (CT) device, a C-arm device, etc.) usually includes an X-ray tube and a detector for transmitting and detecting X-rays, respectively. However, electron scattering in the X-ray tube may cause a defocus of the X-rays. The defocus may cause that the focus of the X-rays is not centered on a spot of a small area, but to form a focus region of a halo-like shape. When a defocused signal passes through an object, the transmission direction of the X-rays may change. Boundaries of an image captured by the medical imaging device may be blurry, thereby generating artifacts. Thus, it is desired to provide systems and methods for image correction by eliminating or reducing artifacts rooted in defocus in an X-ray tube.

SUMMARY

According to a first aspect of the present disclosure, a system for image correction is provided. The system may include at least one storage device including a set of instructions for correcting an image and at least one processor in communication with the at least one storage device. When executing the set of instructions, the at least one processor may be directed to cause the system to perform operations including: obtaining image data of a target object; determining a target image based on the image data; determining a target aspect ratio of the target object in the target image; determining a correction function for correcting artifacts in the target image based on the target aspect ratio; and obtaining a corrected image of the target image by correcting the target image based on the correction function.

In some embodiments, the determining a target aspect ratio of the target object in the target image may include: obtaining a sinogram of the target object based on the image data; determining a plurality of axis lengths of the target object under a plurality of view angles based on the sinogram and a threshold; and determining the target aspect ratio of the target object based on the plurality of axis lengths, wherein the target aspect ratio is a ratio between a maximum axis length and a minimum axis length among the plurality of axis lengths.

In some embodiments, the determining a plurality of axis lengths of the target object under a plurality of view angles based on the sinogram and the threshold may include: for each view angle of the plurality of view angles, obtaining a chord under the view angle based on the sinogram; identifying, on the chord, a first pixel having a first value that exceeds the threshold; identifying, on the chord, a second pixel having a second value that exceeds the threshold; and determining an axis length of the target object under the view angle based on the first pixel, the second pixel, and geometric parameters of a detector that captures the image data.

In some embodiments, the identifying, on the chord, a first pixel having a first value that exceeds the threshold may include: performing a first scan, from a first end of the chord, of the chord along a first direction; and identifying the first pixel that is the first one, during the first scan, whose value exceeds the threshold.

In some embodiments, the identifying, on the chord, a second pixel having a first value that exceeds the threshold may include: performing a second scan, from a second end of the chord, the chord along a second direction that is opposite to the first direction; and identifying the second pixel that is the first one, during the second scan, whose value exceeds the threshold.

In some embodiments, the determining a corrections function for correcting artifacts in the target image based on the target aspect ratio may include: obtaining a reference set including a plurality of reference pairs, each reference pair of the plurality of reference pairs corresponding to a reference aspect ratio and a reference function with respect to the reference aspect ratio; and determining the correction function based on the reference set and the target aspect ratio.

In some embodiments, the reference function is a reference convolution kernel, and the correction function is a correction convolution kernel.

In some embodiments, the obtaining a reference set may include: obtaining a plurality of reference aspect ratios; for each reference aspect ratio of the plurality of reference aspect ratios, obtaining a focus signal distribution and a defocus signal distribution with respect to the reference aspect ratio; and determining the reference function with respect to the reference aspect ratio based on the focus signal distribution and the defocus signal distribution.

In some embodiments, the obtaining a focus signal distribution and a defocus signal distribution with respect to the reference aspect ratio may include: providing a reference object that has the reference aspect ratio; scanning the reference object using a light source, wherein the light source emits a focus signal passing through a focus of the light source and a defocus signal scatting from the focus signal; and obtaining the focus signal distribution and the defocus signal distribution from a detector that captures the target image, wherein the focus signal distribution is obtained from a detecting area corresponding to the focus signal, and the defocus signal distribution is obtained from a detecting area corresponding to the defocus signal.

In some embodiments, the reference object includes at least one of a water phantom, a polymethylmethacrylate (PMMA) phantom, or a nylon phantom.

In some embodiments, the determining the correction function based on the reference set and the target aspect ratio may include: obtaining at least two reference aspect ratios from the reference set based on the target aspect ratio; obtaining at least two reference functions corresponding to the at least two reference aspect ratios; and determining the correction function based on the at least two reference functions.

In some embodiments, a difference between the target aspect ratio and at least one of the at least two reference aspect ratios may be less than a difference threshold.

In some embodiments, the correction function may be determined based on the at least two reference functions using an interpolation algorithm or an extrapolation algorithm.

In some embodiments, the interpolation algorithm may include at least one of a linear interpolation, a high-order interpolation, or a nearest neighbor interpolation.

In some embodiments, the obtaining a corrected image of the target image by correcting the target image based on the correction function may include: determining an original intensity distribution function based on the target image; determining an error function based on the original intensity distribution function and the correction function; determining a corrected intensity distribution based on the original intensity distribution and the error function; and obtaining the corrected image by reconstructing the target image based on the corrected intensity distribution.

According to another aspect of the present disclosure, a method for image correction is provided. The method may include obtaining image data of a target object; determining a target image based on the image data; determining a target aspect ratio of the target object in the target image; determining a correction function for correcting artifacts in the target image based on the target aspect ratio; and obtaining a corrected image of the target image by correcting the target image based on the correction function.

According to still another aspect of the present disclosure, a non-transitory readable medium is provided. The non-transitory readable medium may include at least one set of instructions for processing an X-ray image. When executed by at least one processor of an electrical device, the at least one set of instructions may direct the at least one processor to perform a method including: obtaining image data of a target object; determining a target image based on the image data; determining a target aspect ratio of the target object in the target image; determining a correction function for correcting artifacts in the target image based on the target aspect ratio; and obtaining a corrected image of the target image by correcting the target image based on the correction function.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not scaled. These embodiments are non-limiting exemplary embodiments, in which like reference numerals represent similar structures throughout the several views of the drawings, and wherein.

DETAILED DESCRIPTION

Figure 1:
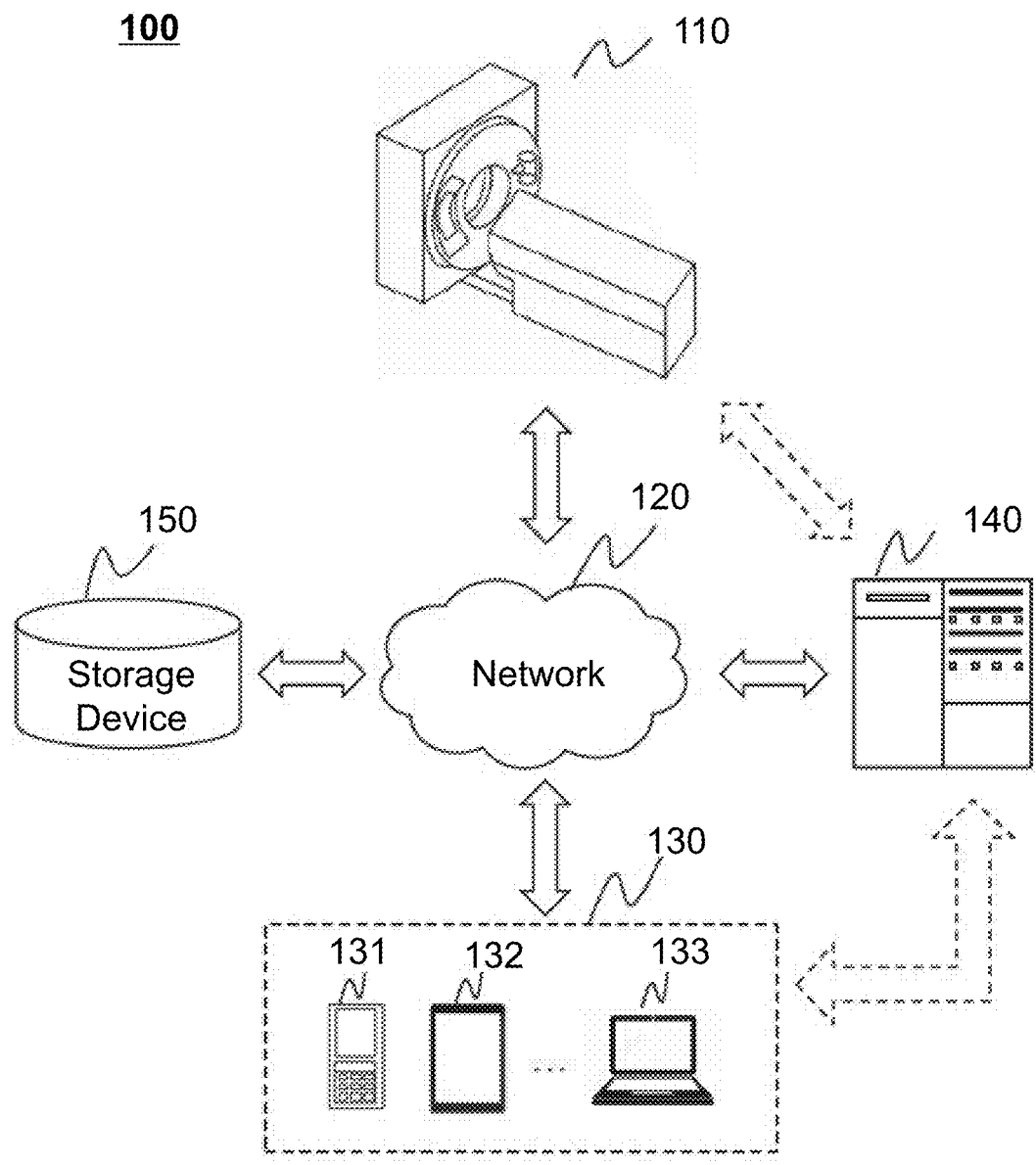
FIG. 1 is a schematic diagram illustrating an exemplary imaging system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules may be callable from other modules/units/blocks or themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and may be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or may be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description regarding the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

One aspect of the present disclosure relates to systems and methods for correcting artifacts in an image. The system and method may correct artifacts caused by defocus in an X-ray tube based on a ratio between a longest route to a shortest route (an aspect ratio) that the X-rays pass through an object. According to the systems and methods, a plurality of aspect ratios of different objects may be statistically calculated and a plurality of reference phantoms may be provided for simulating such different objects. The systems and methods may use an imaging device to scan the reference phantoms or use a computer to simulate the scanning of the reference phantoms to obtain correction functions corresponding to different aspect ratios. The artifacts in an image may be corrected according to the corresponding reference functions and the aspect ratio of the object.

FIG. 1 is a schematic diagram illustrating an exemplary imaging system 100 according to some embodiments of the present disclosure. The imaging system 100 may include an imaging device 110, a network 120, a terminal 130, a processing device 140, and a storage device 150. Components in the imaging system 100 may be connected to each other through the network 120. For example, the imaging device 110 may be connected to or communicate with the terminal 130 through the network 120.

In some embodiments, the imaging device 110 may obtain image data of the object by scanning an object. In some embodiments, the imaging device 110 may be configured to obtain medical image data. The scanned object may be a whole or part of an organ or tissue of a human body or an animal, such as the head, the heart, etc., of a human or an animal. In some embodiments, the imaging device 110 may be configured to obtain industrial image data, and the scanned object may be a workpiece. In some embodiments, the imaging device 110 may be an X-ray imaging device, such as a computed tomography scanner (CT), a C-arm device, or the like, or any combination thereof.

The network 120 may include any suitable network that may facilitate exchange of information and/or data for the imaging system 100. In some embodiments, at least one component of the imaging system 100 (e.g., the imaging device 110, the processing device 140, the storage device 150, the terminal 130) may exchange information and/or data with at least one other components of the imaging system 100 via the network 120. For example, the processing device 140 may obtain an image output from the imaging device 110 via the network 120. As another example, the processing device 140 may obtain a user (e.g., a doctor) instruction from the terminal 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include at least one network access point. For example, the network 120 may include wired and/or wireless network access points such as base stations and/or internet exchange points through which at least one component of the imaging system 100 may be connected to the network 120 to exchange data and/or information.

The terminal 130 may be connected to and/or communicate with the imaging device 110, the processing device 140, and/or the storage device 150. For example, the terminal 130 may obtain an image from the processing device 140. As another example, the terminal 130 may obtain an image obtained by the imaging device 110 and send the image to the processing device 140 for processing. In some embodiments, the terminal 130 may include a mobile device 131, a tablet computer 132, a laptop computer 133, or the like, or any combination thereof. For example, the mobile device 131 may include a mobile phone, personal digital assistance (PDA), a gaming device, a navigation device, a point of sale (POS) device, or the like, or any combination thereof. In some embodiments, the terminal 130 may include an input device, an output device, etc. The input device may include an alphanumeric and other keys. The input device may select keyboard input, touch screen (e.g., with tactile or tactile feedback) input, voice input, eye tracking input, brain monitoring system input, or any other similar input mechanism. The input information received through the input device may be transmitted to the processing device 140 via, for example, a bus, for further processing. Other types of input devices may include a cursor control device, such as a mouse, a trackball, or cursor direction keys, etc. The output device may include a display, a speaker, a printer, or the like, or a combination thereof. In some embodiments, the terminal 130 may be part of the processing device 140.

The processing device 140 may process data and/or information obtained from the imaging device 110, the storage device 150, the terminal 130, or other components of the imaging system 100. For example, the processing device 140 may obtain image data of a target object or a target image of the target object from the imaging device 110. As another example, the processing device 140 may determine a target aspect ratio of the target object and a correction function for correcting artifacts in the target image based on the target aspect ratio. As still another example, the processing device 140 may correct the target image using the correction function. In some embodiments, the processing device 140 may be a single server or a server group. The server group may be centralized or distributed. In some embodiments, the processing device 140 may be local or remote. For example, the processing device 140 may access information and/or data from the imaging device 110, the storage device 150, and/or the terminal 130 via the network 120. As another example, the processing device 140 may be directly connected to the imaging device 110, the terminal 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented by the computing device 200.

The storage device 150 may store data, instructions, and/or any other information. In some embodiments, the storage device 150 may store data obtained from the imaging device 110, the terminal 130, and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. An exemplary volatile read-write memory may include a random access memory (RAM). An exemplary random access memory may include a dynamic random-access memory (DRAM), a double date rate synchronous dynamic random-access memory (DDR SDRAM), a static random-access memory (SRAM), a thyristor random-access memory (T-RAM), and a zero-capacitor random-access memory (Z-RAM), etc. An exemplary read-only memory may include a mask read-only memory (MROM), a programmable read-only memory (PROM), an erasable programmable read-only memory (EPROM), an electrically erasable programmable read-only memory (EEPROM), a compact disk read-only memory (CD-ROM), and a digital versatile disk read-only memory, etc. In some embodiments, storage device 150 may be implemented on a cloud platform.

In some embodiments, the storage device 150 may be connected to the network 120 to communicate with at least one other component of the imaging system 100 (e.g., the processing device 140, the terminal 130). At least one component of the imaging system 100 may access the data or instructions stored in the storage device 150 via the network 120. In some embodiments, the storage device 150 may be part of the processing device 140.

It should be noted that the description is intended to be illustrative, and not to limit the scope of the present disclosure. For persons having ordinary skills in the art, multiple variations and modifications may be made under the teachings of the present disclosure. The features, structures, methods, and other characteristics of the exemplary embodiments described herein may be combined in various ways to obtain additional and/or alternative exemplary embodiments. For example, the storage device 150 may be a data storage including cloud computing platforms, such as a public cloud, a private cloud, a community cloud, and a hybrid cloud, etc. However, those variations and modifications do not depart from the scope of the present disclosure.

It should be noted that the imaging system 100 and relevant modules may be implemented in various ways. For example, the imaging system 100 and relevant modules may be implemented through hardware, software, or a combination of software and hardware. Wherein, the hardware component may be implemented by a dedicated logic, and the software component may be stored in the storage which may be executed by a suitable instruction execution system, for example, a microprocessor or a dedicated design hardware. It will be appreciated by those skilled in the art that the above methods and systems may be implemented by computer-executable instructions and/or embedding in the control codes of a processor. For example, the control codes may be provided by a medium such as a disk, a CD, or a DVD-ROM, a programmable memory device such as read-only memory (e.g., firmware), or a data carrier such as an optical or electric signal carrier. The imaging system 100 and relevant modules of the present disclosure may be implemented by hardware circuits, e.g., very large-scale integrated circuits or gate arrays, semiconductors such as logic chips or transistors, programmable hardware devices such as field-programmable gate arrays or programmable logic devices, etc. The imaging system 100 and relevant modules may be implemented by software executed by various processors. The imaging system 100 and relevant modules may also be implemented by a combination (e.g., firmware) of the hardware circuits and the software.

Figure 2:
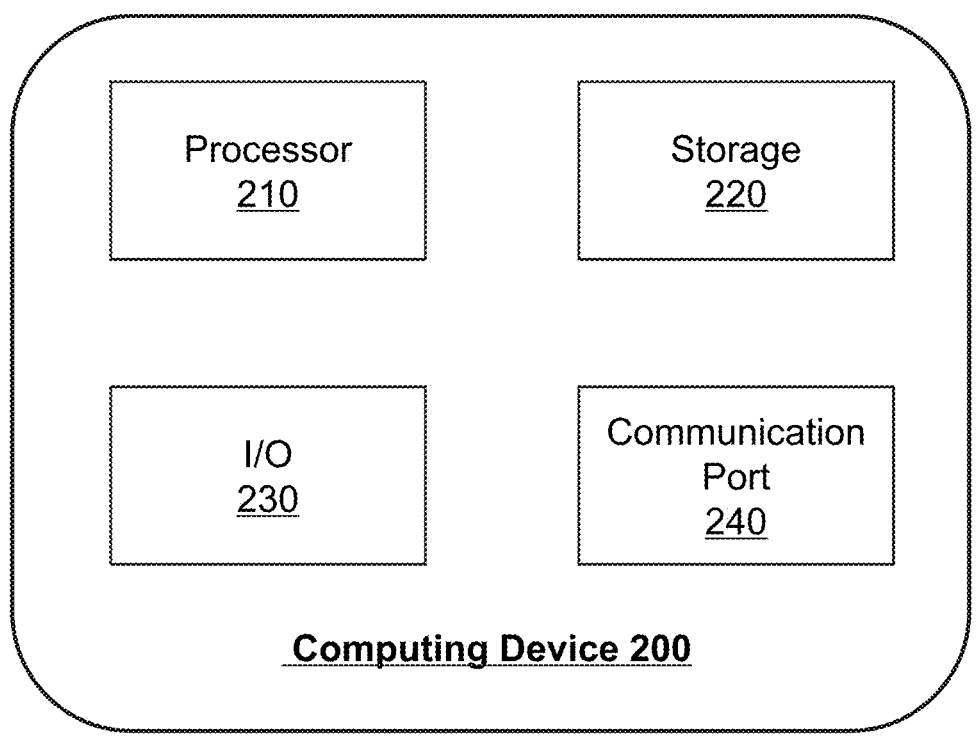
FIG. 2 is a schematic diagram illustrating hardware and/or software components of an exemplary computing device according to some embodiments of the present disclosure.

FIG. 2 is a schematic diagram illustrating exemplary hardware and/or software components of an exemplary computing device 200 according to some embodiments of the present disclosure. The computing device 200 may include a processor 210, a storage device 220, an input/output (I/O) 230, and a communication port 240.

The processor 210 may execute computer instructions (e.g., program codes) and perform functions of the processing device 140 in accordance with techniques described herein. The computer instructions may include, for example, routines, programs, objects, components, data structures, procedures, modules, and functions, which perform particular functions described herein. For example, the processor 210 may process data of the imaging device 110, the terminal 130, the storage device 150, and/or any other components of the imaging system 100. In some embodiments, the processor 210 may include at least one hardware processors, such as a microcontroller, a microprocessor, a reduced instruction set computer (RISC), an application-specific integrated circuit (ASIC), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors, and thus operations and/or method operations that are performed by one processor as described in the present disclosure may also be jointly or separately performed by the multiple processors. For example, if in the present disclosure the processor of the computing device 200 executes both operations A and operations B, it should be understood that operation A and operation B may also be performed jointly or separately by two or more different processors in the computing device 200 (e.g., a first processor executes operation A and a second processor executes operation B, or the first and second processors jointly execute operations A and B).

The storage device 220 may store data/information obtained from the imaging device 110, the terminal 130, the storage device 150, and/or any other component of the imaging system 100. In some embodiments, the storage device 220 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The random access memory may include a dynamic random access memory (DRAM), a double date rate synchronous dynamic random access memory (DDRS DRAM), a static random access memory (SRAM), a thyristor random access memory (T-RAM), and a zero-capacitor (Z-RAM), etc. An exemplary read-only memory may include a mask read-only memory (MROM), a programmable read-only memory (PROM), an erasable programmable read-only memory (EPROM), an electrically erasable programmable read-only memory (EEPROM), a compact disk read-only memory (CD-ROM), and a digital versatile disk read-only memory, etc. In some embodiments, the storage device 220 may store at least one program and/or instructions to perform exemplary methods described in the present disclosure.

The I/O 230 may be configured to input and/or output signals, data, information, etc. In some embodiments, the I/O 230 may enable user interaction with the processing device 140. In some embodiments, the I/O 230 may include an input device and an output device. An exemplary input device may include a keyboard, a mouse, a touch screen, a microphone, or the like, or any combination thereof. An exemplary output device may include a display device, a loudspeaker, a printer, a projector, or the like, or any combination thereof. An exemplary display device may include a liquid crystal display (LCD), a light-emitting diode (LED)-based display, a flat panel display, a curved screen, a television device, a cathode ray tube, or the like, or a combination thereof.

The communication port 240 may be connected to a network (e.g., the network 120) to facilitate data communications. The communication port 240 may establish connections between the processing device 140 and the imaging device 110, the terminal 130, and/or the storage device 150. The connection may include a wired connection or a wireless connection. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or any combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
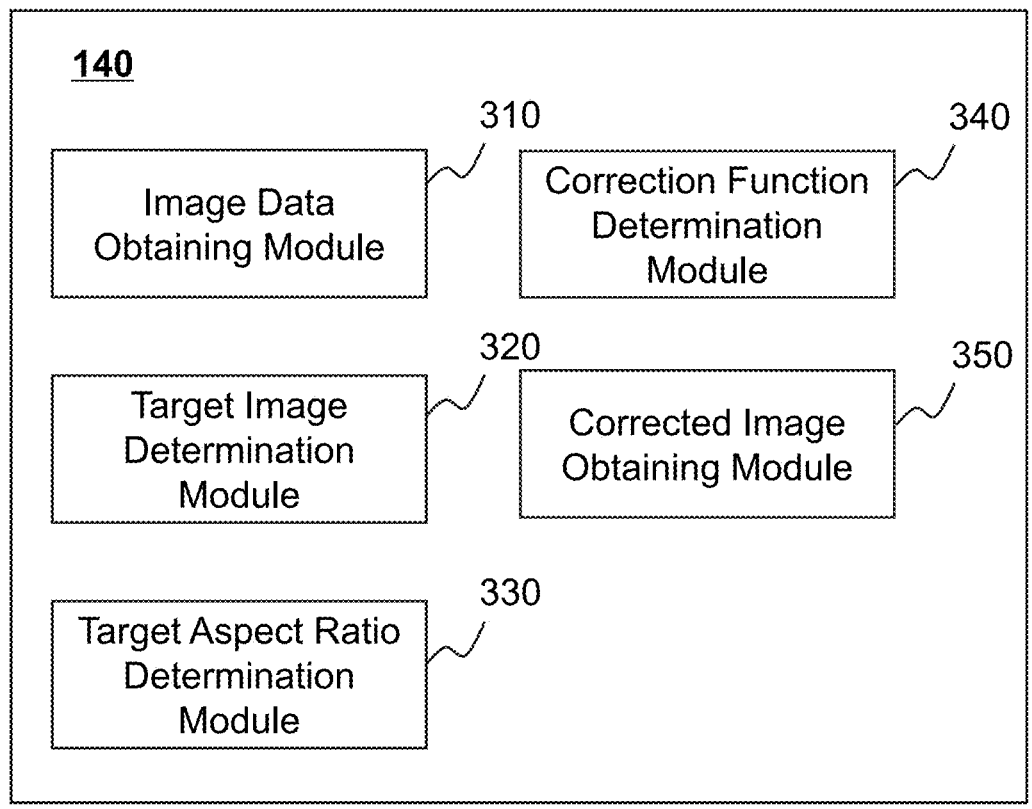
FIG. 3 is a block diagram illustrating an exemplary processing device according to some embodiments of the present disclosure.

FIG. 3 is a block diagram illustrating an exemplary processing device according to some embodiments of the present disclosure. As shown in FIG. 3, the processing device 140 may include an image data obtaining module 310, a target image determination module 320, a target aspect ratio determination module 330, a correction function determination module 340, and a corrected image obtaining module 350.

The image data obtaining module 310 may be configured to obtain image data of a target object. In some embodiments, the image data may include any data used to generate an image. The image data may carry information about the target object.

The target image determination module 320 may be configured to determine a target image based on the image data. In some embodiments, the target image determination module 320 may process the image data to obtain the target image. The target image may be an image in any specific display mode.

The target aspect ratio determination module 330 may be configured to determine a target aspect ratio of the target object in the target image. In some embodiments, the target aspect ratio may reflect a size and/or a shape of the target object. In some embodiments, the target aspect ratio may be a ratio of a maximum traverse length to a minimum traverse length that the signal passes through the target object. For example, the target aspect ratio determination module 330 may obtain a sinogram of the target object based on the image data. As another example, the target aspect ratio determination module 330 may determine a plurality of axis lengths of the target object from a plurality of view angles based on the sinogram and a threshold of a pixel (or a voxel pixel). As still another example, the target aspect ratio determination module 330 may determine the target aspect ratio of the target object based on the plurality of axis lengths. In some embodiments, the target aspect ratio is a ratio of a maximum axis length to a minimum axis length among the plurality of axis lengths.

The correction function determination module 340 may be configured to determine a correction function for correcting artifacts in the target image based on the target aspect ratio. In some embodiments, the correction function may be in the form of an algorithm, a formula, a weight, a coefficient, etc., for correcting artifacts in the target image. In some embodiments, the correction function determination module 340 may obtain a reference set including a plurality of reference pairs. Each reference pair of the plurality of reference pairs may include a reference aspect ratio and a reference function with respect to the reference aspect ratio. In some embodiments, the correction function determination module 340 may determine the correction function based on the reference set and the target aspect ratio.

The corrected image obtaining module 350 may be configured to obtain a corrected image of the target image. For example, the corrected image obtaining module 350 may correct the target image based on the correction function to obtain the corrected image.

Figure 4:
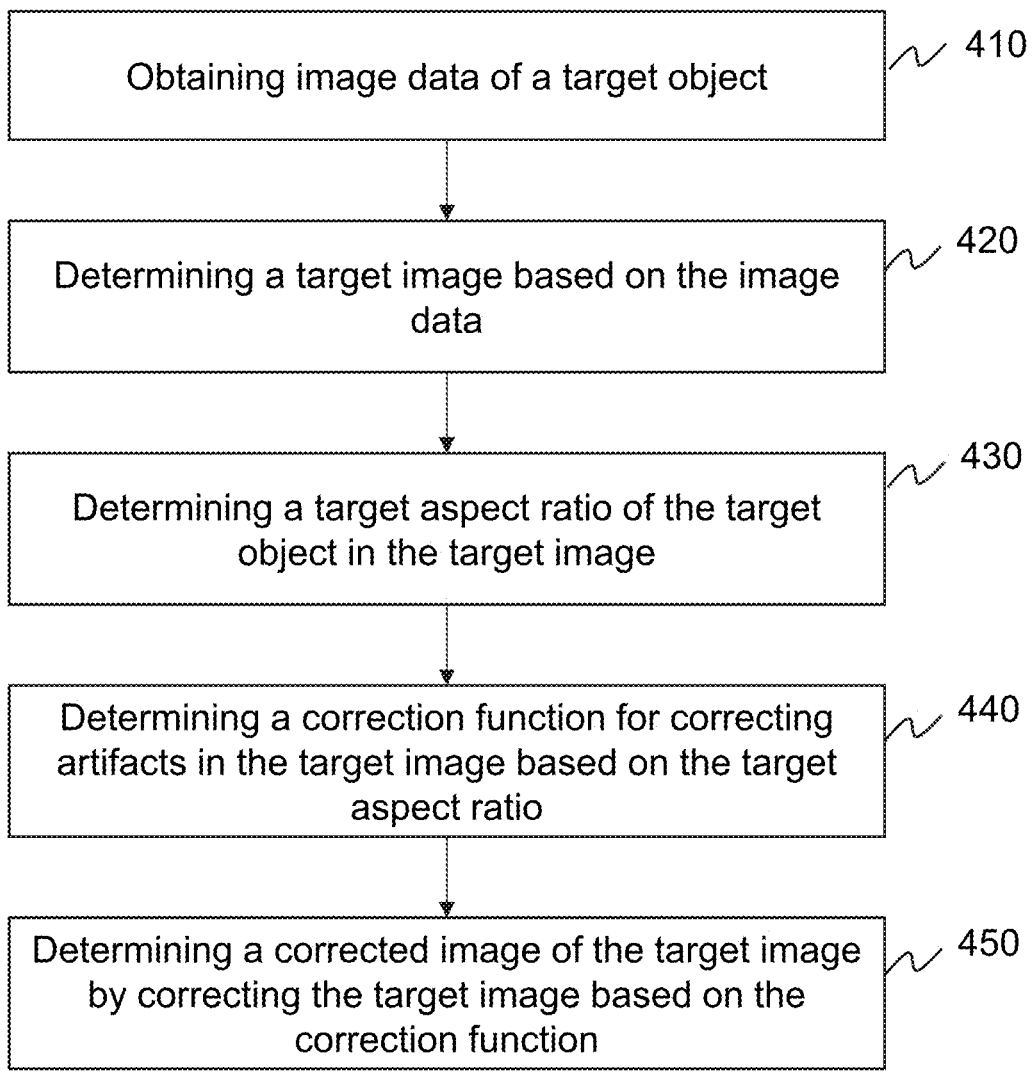
FIG. 4 is an exemplary flowchart illustrating an image correction process according to some embodiments of the present disclosure.

More descriptions regarding the operations performed by the modules in FIG. 4 may be found elsewhere (e.g., FIGS. 4, 9, and 11) in the present disclosure. It should be noted that the above description of the processing device 140 and relevant modules is for convenience of description only, and cannot limit the present disclosure to be within the scope of the illustrated embodiment. For persons having ordinary skills in the art, modules may be combined in various ways or connected with other modules as sub-systems, and various modifications and transformations in form and detail may be conducted under the teaching of the present disclosure. For example, the target aspect ratio determination module 330 may be divided into two or more units to determine the target aspect ratio. Such modification is within the protection scope of the present disclosure. In some embodiments, the processing device 140 may further include one or more additional modules, such as a storage module.

FIG. 4 is an exemplary flowchart illustrating an image correction process 400 according to some embodiments of the present disclosure. In some embodiments, the process 400 may be implemented as a set of instructions (e.g., an application) stored in the storage device 150 or the storage device 220. The processing device 140 and/or the processor 210 may execute the set of instructions, and when executing the instructions, the processing device 140 and/or the processor 210 may be configured to perform the process 400. The operations of the illustrated process presented below are intended to be illustrative. In some embodiments, the process 400 may be accomplished with one or more additional operations not described and/or without one or more of the operations discussed. Additionally, the order of the operations of the process 400 illustrated in FIG. 4 and described below is not intended to be limiting.

In 410, the processing device 140 (e.g., the processor 210, the image data obtaining module 310) may obtain image data of a target object.

In some embodiments, the target object may include a human body or a portion thereof. For example, the target object may include an organ or a body part of a human. In some embodiments, the organ may include the heart, the liver, a lung, the stomach, a kidney, or the like, or any combination thereof, of a human. In some embodiments, the body part may include the head, a hand, an arm, a foot, a calf, a thigh, the abdomen, the chest, the cervical spine, or the like, or any combination thereof, of a human.

In some embodiments, the image data may include any data used to generate an image. The image data may carry information about the target object. In some embodiments, the imaging device 110 may scan the target object using X-rays to obtain scanned data of the target object and send the scanned data to the processing device 140. The processing device 140 may process the scanned data. In some embodiments, the processing device 140 may process the scanned data to generate image data in a format that meets specific needs. For example, the processing device 140 may process the scanned data to generate the image data that may in turn be used to generate an image in a specific display mode (e.g., a target image of the target object, a sinogram of the target object).

In 420, the processing device 140 (e.g., the processor 210, the target image determination module 320) may determine a target image based on the image data.

In some embodiments, the target image may be an image in any specific display mode. In some embodiments, the processing device 140 may process the image data (e.g., correct the image data, reconstruct the image data, etc.) to obtain the target image.

Figure 5:
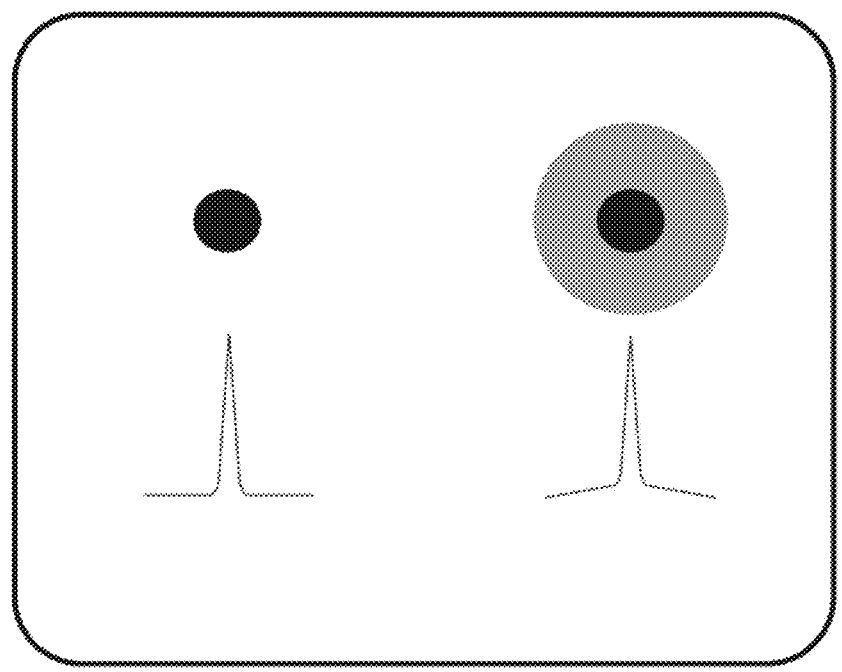
FIG. 5 is schematic diagram illustrating an exemplary focused signal and an exemplary defocused signal according to some embodiments of the present disclosure.

FIG. 5 are schematic diagrams illustrating an exemplary focused signal and an exemplary defocused signal according to some embodiments of the present disclosure. In some embodiments, a radiation source (e.g., an X-ray source, an X-ray tube, etc.) of the imaging device 110 may emit X-rays. Electron scattering in the radiation source (e.g., X-ray tube) may cause defocus with respect to a focus of the X-ray tube. The X-rays emitted from the X-ray tube may be not centered on a spot of a small area (as shown on the top-left of FIG. 5), but to form a halo-like pattern (as shown on the top-right of FIG. 5). A focused signal is illustrated by the curve at the bottom-left of FIG. 5 in which the curve has two essentially flat tails. A defocused signal is illustrated by the curve at the bottom-right of FIG. 5 in which the curve has two gradually changing tails.

Figure 6:
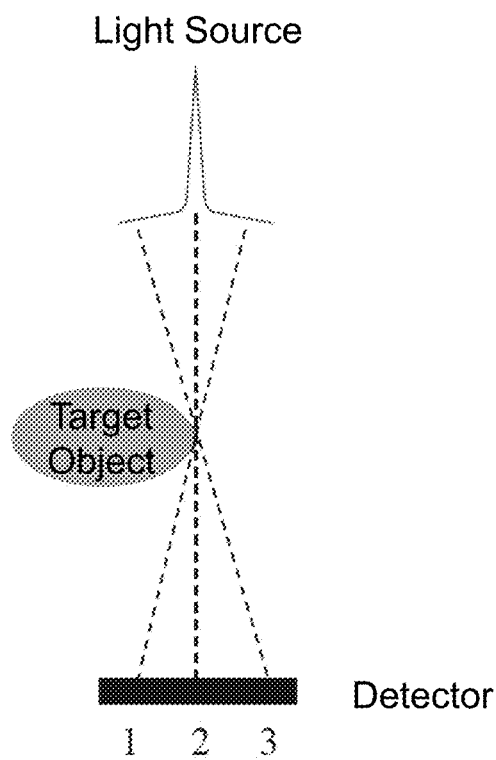
FIG. 6 is a schematic diagram illustrating an exemplary imaging device according to some embodiments of the present disclosure.

FIG. 6 is a schematic diagram illustrating an exemplary imaging device according to some embodiments of the present disclosure. In some embodiments, the imaging device may include a radiation source (e.g., an X-ray source, an X-ray tube, etc.) and a detector. The radiation source may emit a focused signal passing through a focus of the radiation source and a defocused signal scatted from the focused signal. The focused signal may impinge on region 2 of the detector (or pixel 2 on the detector) after passing through the boundary of the target object. The defocused signal may pass through the target object and impinge on region 1 of the detector (or pixel 1 on the detector) and/or region 3 of the detector (or pixel 3 on the detector). Artifacts caused by the defocused signal may be generated on or around the boundary of the target object. In some embodiments, if a target aspect ratio of the target object is great (e.g., greater than a ratio threshold), the artifact may be directional as shown in FIG. 7.

Figure 7:
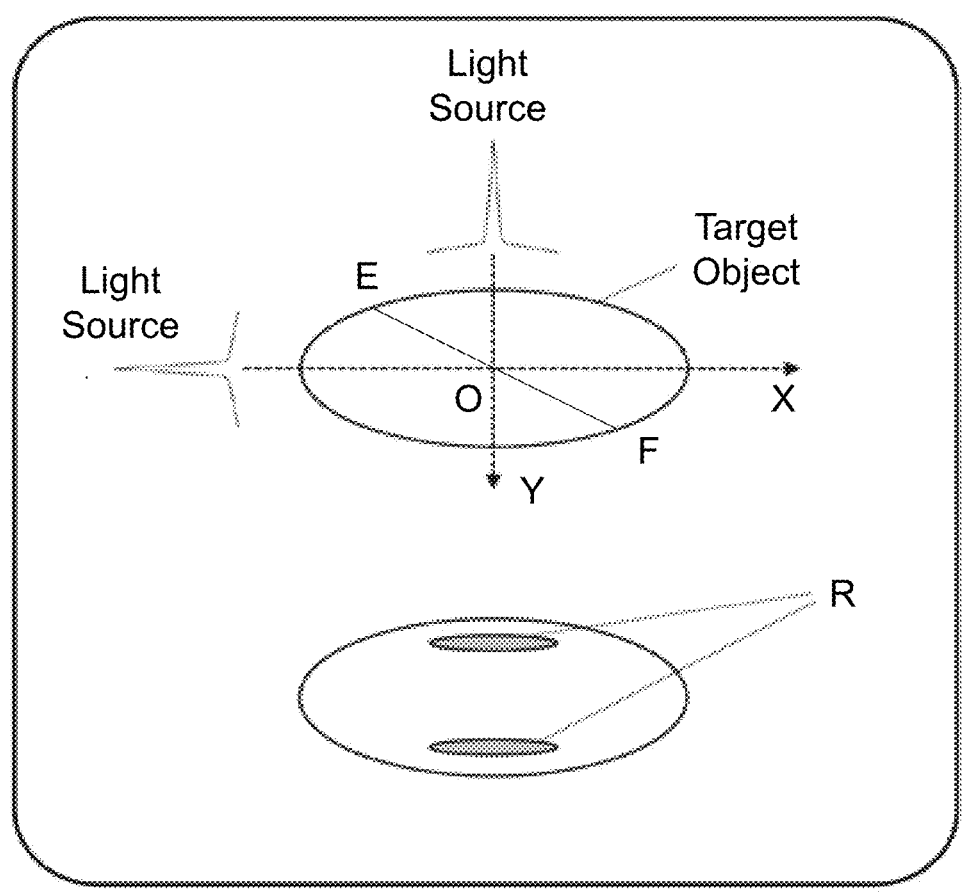
FIG. 7 is schematic diagram illustrating exemplary scanning directions on a target object and an exemplary target image showing artifacts on the target object according to some embodiments of the present disclosure.

FIG. 7 are schematic diagrams illustrating exemplary scanning directions on a target object and an exemplary target image showing artifacts in an image of the target object according to some embodiments of the present disclosure. A cross-section of the target object may have a long axis (e.g., the X-axis illustrated in FIG. 7) and a short axis (e.g., the Y-axis illustrated in FIG. 7). As shown on the top of FIG. 7, the X-rays emitted from the radiation source may traverse the target object along a direction of a long axis (X-axis) or a direction of a short axis (Y-axis). Artifacts in the target image is shown on the bottom of FIG. 7. In some embodiments, when a signal (including the focused signal and the defocused signal) traverses the target object along the short axis and the long axis of the target object, respectively, the probability of scattering occurs may be lower when the traverse path is short than when the scanning path is long. The defocused signal may be less affected by scattering when the traverse path is short than when the traverse path is long. Therefore, artifacts may be directional. For example, the artifacts may be distributed along boundaries along the long axis (X-axis as shown in FIG. 7). The regions R as shown in FIG. 7 may have a high probability of including artifacts. In some embodiments, the shape of an artifact region may have the shape of an ellipse, a bar, a circle, a rectangular, or other irregular shapes, or the like, or any combination thereof.

In 430, the processing device 140 (e.g., the processor 210, the target aspect ratio determination module 330) may determine a target aspect ratio of the target object in the target image.

In some embodiments, the target aspect ratio may reflect a size and/or a shape of the target object. In some embodiments, the target aspect ratio may be a ratio of a maximum traverse length to a minimum traverse length that the signal passes through the target object. For example, the maximum traverse length may be a length of a maximum scanning path that a signal emitting from the imaging device 110 passes through the target object. The minimum traverse length may be a length of a minimum scanning path that the signal passes through the target object. In some embodiments, the imaging device 110 may scan the target object by rotating around the target object. The target aspect ratio may be a ratio of a maximum axis length to a minimum axis length on a cross-section profile of the target object. In some embodiments, the cross-section profile may be perpendicular to a rotation plane of a gantry of the imaging device 110. As shown in FIG. 7, the cross-section profile may be on an XY plane. In some embodiments, an axis length may be a length of a line segment (e.g., a line segment EF as shown in FIG. 7) that has both ends (e.g., an end E and an end F) on the cross-sectional profile (on the XY plane) of the target object and passes through the center (e.g., a point O) of the cross-section profile of target object.

In some embodiments, the processing device 140 may determine the target aspect ratio of the target object in the target image based on the obtained image data. For example, the processing device 140 may obtain a sinogram of the target object based on the image data. The sinogram may be obtained by scanning the target using the imaging device 110 from a plurality of view angles. The processing device 140 may determine a plurality of axis lengths of the target object from the plurality of view angles based on the sinogram and a threshold of a pixel (or a voxel pixel). For example, the processing device 140 may determine a boundary between the target object and its surroundings (e.g., air and other objects) in the sinogram acquired from a view angle based on the threshold. The processing device 140 may determine an axis length of the target object of each view angle according to the boundary corresponding to the view angle. The processing device 140 may obtain a maximum axis length and a minimum axis length from a plurality of axis lengths determined from the boundaries corresponding to the plurality of view angles, and determine that the ratio of the maximum axis length to the minimum axis length as the target aspect ratio of the target object. For example, the target aspect ratio may be 1:1, 1.5:1, 2:1, etc. More descriptions regarding the determination of the target object aspect ratio may be found elsewhere (e.g., FIG. 9 and the descriptions thereof) in the present disclosure.

In 440, the processing device 140 (e.g., the processor 210, the correction function determination module 340) may determine a correction function for correcting artifacts in the target image based on the target aspect ratio.

In some embodiments, the correction function may be in the form of an algorithm, a formula, a weight, a coefficient, etc., for correcting artifacts in the target image. For example, the correction function may be a corrected convolution kernel. In some embodiments, the processing device 140 may use the correction function to perform corresponding processing on the target image to correct artifacts in the target image.

In some embodiments, the processing device 140 may determine the correction function based on the target aspect ratio of the target object. In some embodiments, the processing device 140 may retrieve a reference set from the storage device (e.g., the storage device 150 and/or the storage device 220). The reference set may include a plurality of reference pairs. A reference pair may include a reference aspect ratio and a reference function with respect to the reference aspect ratio. As used herein, a reference function refers to one that is configured to correct artifacts in an image acquired by a same or similar imaging device (e.g., the imaging device 110) caused by defocusing of the radiation source (or the X-ray source) of the imaging device. The processing device 140 may determine the correction function based on the reference set and the target aspect ratio. For example, the processing device 140 may select one or more reference pairs whose reference aspect ratios are within a range from the target aspect ratio such that the difference between the target aspect ratio and the reference aspect ratio of any one of the selected one or more reference pairs is less than a difference threshold. The processing device 140 may obtain the one or more reference functions paired with the one or more reference aspect ratios. The processing device 140 may determine the correction function by performing an algorithm (e.g., an interpolation algorithm, an extrapolation algorithm, etc.) on the one or more reference functions.

In some embodiments, the processing device 140 may obtain a machine learning model from the storage device (e.g., the storage device 150 and/or the storage device 220). The machine learning model may predict the correction function based on the target aspect ratio of the target object. For example, the machine learning model may be obtained by training based on a plurality of reference aspect ratios of a plurality of reference objects and corresponding reference functions. The processing device 140 may input the target aspect ratio into the machine learning model, and the output of the machine learning model may be the correction function. More descriptions regarding the determination of the correction function may be found elsewhere (e.g., FIG. 9 and the descriptions thereof) in the present disclosure.

In 450, the processing device 140 (e.g., the processor 210, the corrected image obtaining module 350) may obtain a corrected image of the target image by correcting the target image based on the correction function.

In some embodiments, the processing device 140 may determine an original intensity distribution function based on the target image. The original intensity distribution function may represent a signal intensity distribution in the target image. In some embodiments, the processing device 140 may obtain a projection distribution function of the signal emitted by the radiation source on a continuous detector centered on a channel i (e.g., the detector at the positions corresponding to 1-3 as shown in FIG. 6) after passing through the target object. The processing device 140 may determine the original intensity distribution function based on the projection distribution function. For example, the processing device 140 may determine the original intensity distribution function according to the Equation (1):

$$I_O = \text{EXP}(-P) \quad (1),$$

where P denotes the projection distribution function of a signal impinging on the continuous detector that is centered on the channel i after the signal has traversed the target object, and $I_O$ denotes the original intensity distribution function of the signal detected by the detector where the signal does not traverse the target object.

In some embodiments, the processing device 140 may determine an error function based on the original intensity distribution function and the correction function. In some embodiments, the error function may be an intensity distribution corresponding to the artifacts caused by defocusing of the radiation source (or the X-ray source). In some embodiments, the error function may be calculated according to Equation (2):

$$I_S = I_O * K_O \quad (2),$$

where $I_S$ denotes the error function corresponding to the target image, $I_O$ denotes the original intensity distribution function of the signal detected by the continuous detector where the signal does not traverse the target object, and $K_O$ denotes the correction function. For example, $K_O$ denotes a correction convolution kernel.

In some embodiments, the processing device 140 may determine the corrected intensity distribution based on the original intensity distribution function and the error function. In some embodiments, the processing device 140 may determine the corrected intensity distribution according to Equation (3):

$$I_{corr} = I_O - \text{SUM}(I_S) \quad (3),$$

where $I_{corr}$ denotes the corrected intensity distribution of the target image, $I_O$ denotes the original intensity distribution function, and $I_S$ denotes the error function corresponding to the target image.

In some embodiments, the processing device 140 may reconstruct the target image based on the corrected intensity distribution to obtain a corrected image. For example, the processing device 140 may convert the corrected intensity distribution into a corrected projection distribution function. In some embodiments, the corrected projection function may be configured to reconstruct the target image after eliminating or reducing the artifacts caused by defocusing of the radiation source (or the X-ray source). The corrected projection function may indicate a distribution function of a focused signal (without defocusing of the radiation source) impinging on the continuous detector. In some embodiments, the corrected projection function may be calculated according to Equation (4):

$$P_{corr} = -\ln(I_{corr}) \quad (4),$$

where $P_{corr}$ denotes the corrected projection distribution function corresponding to the projection distribution function, and $I_{corr}$ denotes the corrected intensity distribution of the focused signal (without defocusing of the radiation source) impinging on the continuous detector.

Figure 8:
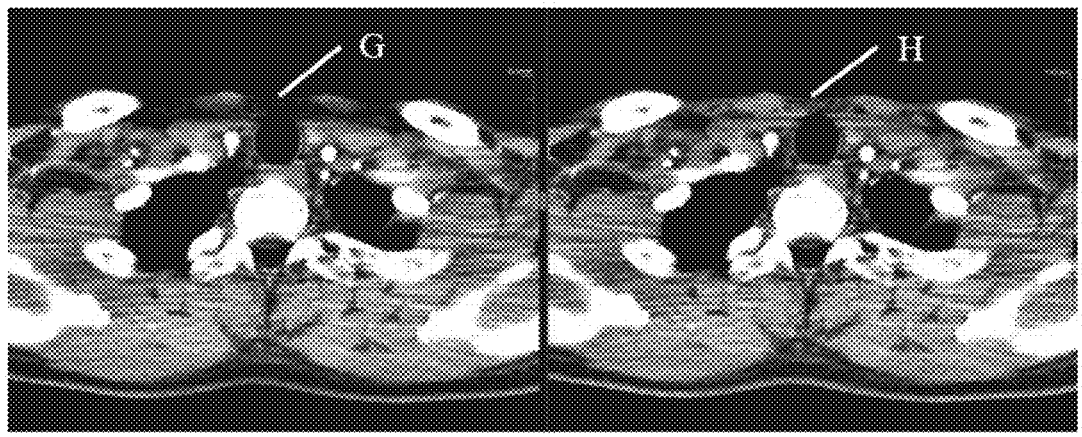
FIG. 8 is a comparison diagram illustrating exemplary images before and after an image correction according to some embodiments of the present disclosure.

FIG. 8 is a comparison diagram illustrating exemplary images before and after an image correction according to some embodiments of the present disclosure. As shown in FIG. 8, G region of a target image has artifacts. H region is obtained after correcting the target image according to the image correction process described in the present disclosure. As shown in FIG. 8, H region has a better contrast and higher image quality than G region. The image correction process according to the present disclosure may effectively reduce or remove defocus artifacts.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 410 and operation 420 may be combined into a single operation. As another example, one or more other optional operations (e.g., a storing operation) may be added elsewhere in the process 400. In the storing operation, the processing device 140 may cause information and/or data (e.g., the image data, the target image, etc.) to be stored in a storage device (e.g., the storage device 150) disclosed elsewhere in the present disclosure.

Figure 9:
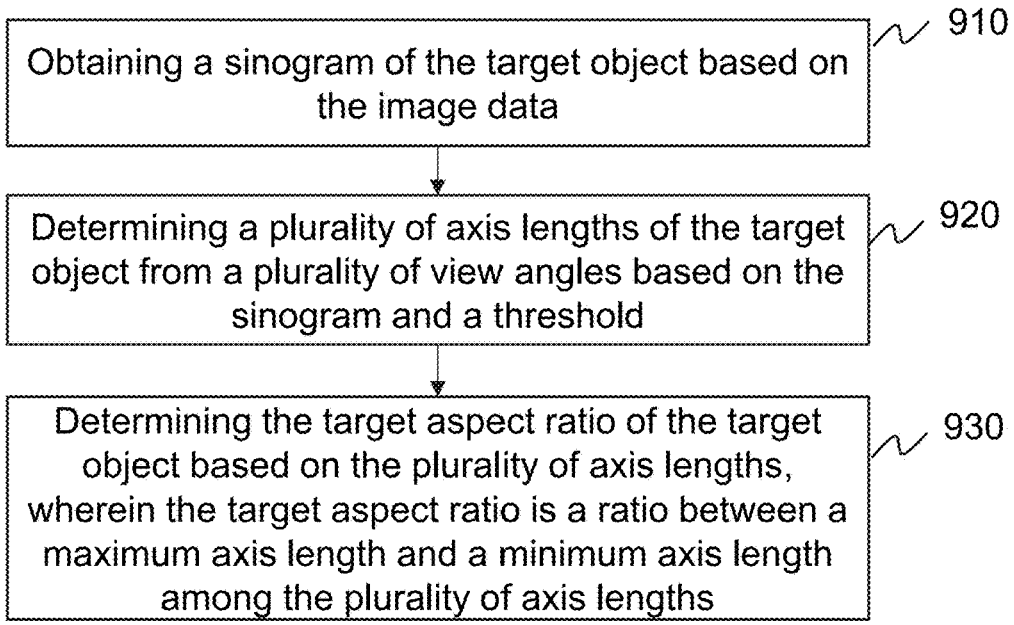
FIG. 9 is a flowchart illustrating an exemplary process for determining a target aspect ratio of a target object according to some embodiments of the present disclosure.

FIG. 9 is a flowchart illustrating an exemplary process 900 for determining a target aspect ratio of a target object according to some embodiments of the present disclosure. In some embodiments, the process 900 may be implemented as a set of instructions (e.g., an application) stored in the storage device 150 or the storage device 220. The processing device 140 and/or the processor 210 may execute the set of instructions, and when executing the instructions, the processing device 140 and/or the processor 210 may be configured to perform the process 900. The operations of the illustrated process presented below are intended to be illustrative. In some embodiments, the process 900 may be accomplished with one or more additional operations not described and/or without one or more of the operations discussed. Additionally, the order of the operations of the process 900 illustrated in FIG. 9 and described below is not intended to be limiting.

In 910, the processing device 140 (e.g., the processor 210, the target aspect ratio determination module 330) may obtain a sinogram of the target object based on the image data.

Figure 10:
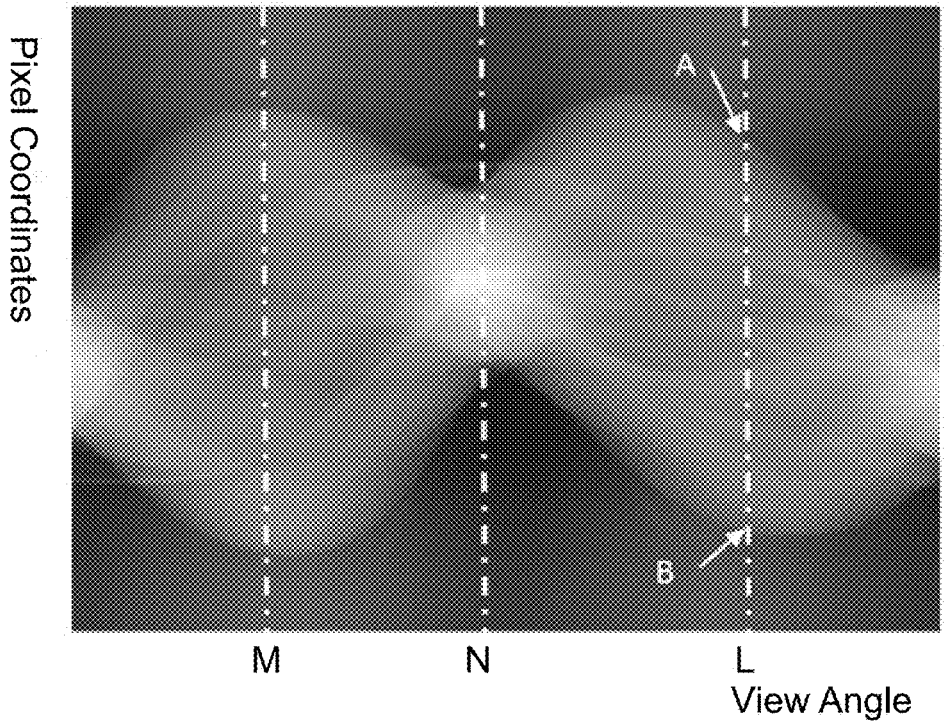
FIG. 10 is a schematic diagram illustrating an exemplary sinogram of an object according to some embodiments of the present disclosure.

In some embodiments, the sinogram of the target object may show a contour of the target object as a sinusoidal shape. The sinogram may be obtained by rotationally scanning the target object from a plurality of view angles using the imaging device 110 that is configured to rotate around the target object. FIG. 10 is a diagram illustrating an exemplary sinogram according to some embodiments of the present disclosure. As shown in FIG. 10, the contour of the target object in the sinogram may be sinusoidal. In some embodiments, the sinogram of the target object may be obtained by scanning the target object in real-time. For example, the imaging device 110 may rotationally scan the target object to obtain the image data of the target object. The processing device 140 may reconstruct the sinogram based on the image data. In some embodiments, the processing device 140 may obtain the sinogram from a storage device (e.g., the storage device 150, the storage device 220).

In 920, the processing device 140 (e.g., the processor 210, the target aspect ratio determination module 330) may determine a plurality of axis lengths of the target object from a plurality of view angles based on the sinogram and a threshold of a pixel (or a voxel pixel).

In some embodiments, the threshold may be a predetermined value used to distinguish different parts (e.g., an organ, a tissue, a body part, air, etc.) in the sinogram. In some embodiments, the threshold may be a value (e.g., a value of a pixel, a value of a voxel pixel, etc.) for represent a characteristic of a pixel in the sinogram. In some embodiments, the threshold may be determined by a machine learning model or a statistical algorithm. For example, the processing device 140 may input the sinogram into the machine learning model. The machine learning model may output the threshold. The machine learning model may be trained based on samples including a plurality of historical sinograms and historical thresholds corresponding to the historical sinograms. As used herein, a historical sinogram or threshold indicates that the sinogram or threshold was obtained from a prior measurement or determination. As another example, an average value of historical thresholds of samples including historical sinograms and the historical thresholds may be designated as the threshold.

In some embodiments, the threshold may be a non-air threshold. The non-air threshold may be used to distinguish a background region from an imaging region of the target object in the sinogram. For example, as shown in FIG. 10, a black region may be the background region, and a white region may be the imaging region corresponding to the target object.

In some embodiments, the processing device 140 may determine the contour of the target object based on the sinogram and the threshold. In some embodiments, the processing device 140 may determine the plurality of axis lengths of the target object along the plurality of view angles based on the contour of the target object. In some embodiments, the view angles may be angles from which the imaging device 110 delivers an X-ray toward the target object during a 360-degree rotation around the target object.

In some embodiments, the plurality of axis lengths in the sinogram along the plurality of view angles may be determined based on pixel coordinates and geometric parameters of the imaging device 110. In some embodiments, the processing device 140 may obtain a chord for each one of many view angles based on the sinogram. For example, as shown in FIG. 10, the horizontal axis may represent view angles, and the vertical axis may represent pixel coordinates along a direction of detector channels (e.g., a direction along pixels in a row of a multirow detector CT). In some embodiments, the chord may be a straight line in the sinogram along the direction of the detector channels for a certain view angle. For example, the dash dotted lines illustrate chords corresponding to view angles M, N, or L as shown in FIG. 10.

In some embodiments, the processing device 140 may identify a first pixel having a first value that exceeds the threshold on a chord. In some embodiments, the first value may be a pixel value of a pixel, a gray value of the pixel, etc. The corresponding threshold may be a corresponding pixel threshold, a corresponding gray value threshold, etc. In some embodiments, the processing device 140 may perform a first scan of the chord along a first direction (e.g., the direction of the detector channels) from a first end of the chord (e.g., the upper end of the sinogram shown in FIG. 10). The processing device 140 may identify the first pixel that is the first one on the chord along that direction whose value exceeds the threshold during the first scan. For example, the processing device 140 may identify a pixel position of the first pixel.

In some embodiments, the processing device 140 may identify a second pixel having a second value that exceeds the threshold on the chord. In some embodiments, the second value may be a pixel value of a pixel, a gray value of the pixel, etc. In some embodiments, the processing device 140 may perform a second scan of the chord along a second direction (e.g., along a direction opposite to the direction of the detector channels) from a second end of the chord (e.g., the lower end of the sinogram shown in FIG. 10). The second direction may be opposite to the first direction. The processing device 140 may identify the second pixel that is the first one whose value exceeds the threshold during the second scan. For example, the processing device 140 may identify a pixel position of the second pixel.

In some embodiments, the processing device 140 may determine the axis length of the target object of the view angle based on the first pixel, the second pixel, and the geometric parameters of the detector that has detected the signals used to generate the target image. In some embodiments, the geometric parameters of the detector may be a pixel size of the detector. For example, if the threshold is a non-air threshold, the processing device 140 may sequentially check pixels along the direction of the detector channels to determine coordinates of the first pixel that is the first one whose value exceeds the non-air threshold. The processing device 140 may sequentially check pixels along the direction opposite to the direction of the detector channels to determine coordinates of the second pixel that is the first one whose value exceeds the non-air threshold. In some embodiments, the coordinates of the first pixel and the coordinates of the second pixel may correspond to the number or count of the detector pixels checked during the first or second scan of the chord. In some embodiments, the processing device 140 may determine the axis length of the target object based on the coordinates of the first pixel, the coordinates of the second pixel, and the pixel size of the detector.

As shown in FIG. 10, the processing device 140 may select a chord corresponding to the view angle L. The processing device 140 may sequentially check pixels on the chord from top to bottom of the chord in the sinogram to identify the first pixel that is the first one whose value exceeds the non-air threshold. The first pixels may be denoted as a point A. The processing device 140 may obtain coordinates of the point A. The processing device 140 may sequentially check pixels on the chord from bottom to top of the chord in the sinogram to identify the second pixel that is the first one whose value exceeds the non-air threshold. The second pixel may be denoted as a point B. The processing device 140 may obtain coordinates of the point B. For example, the coordinates of point A may be denoted as D1 and the coordinates of point B may be denoted as D2. The processing device 140 may determine the axis length of the target object under the view angle L according to Equation (5):

$$L=(D_2-D_1)\times \text{DetSize} \times SID/SDD \qquad (5),$$

where L denotes the axis length of the target object along the view angle L, DetSize denotes the pixel size of the detector, SID denotes a distance from a focus of the radiations source (or the X-ray source) to a rotation center of the imaging device 110, and SDD denotes a distance from a focus of the radiation source to the detector of the imaging device 110.

In some embodiments, the processing device 140 may traverse pixels on the chord from top to bottom of the chord in the sinogram and from bottom to top of the sinogram sequentially for each view angle, and determine the axis length of the target object in the sinogram for each view angle based on coordinates of the identified first pixels, coordinates of the identified second pixels, and the geometric parameters of the imaging device 110.

In 930, the processing device 140 (e.g., the processor 210, the target aspect ratio determination module 330) may determine the target aspect ratio of the target object based on the plurality of axis lengths. In some embodiments, the target aspect ratio may be a ratio of a maximum axis length to a minimum axis length among the plurality of axis lengths.

The plurality of axis lengths of the target object may include the maximum axis length and the minimum axis length. The maximum axis length may have the maximum value among the axis lengths of the target object in the sinogram of all view angles. The minimum axis length may have the minimum value among the axis lengths of the target object in the sinogram of all view angles. In some embodiments, the processing device 140 may obtain the maximum axis length and the minimum axis length by ranking the plurality of axis lengths of the target object. For example, the processing device 140 may generate a ranking result by ranking the axis lengths of the target object under the view angles. The maximum value in the ranking result may be the maximum axis length, and the minimum value in the ranking result may be the minimum axis length. As shown in FIG. 10, the processing device 140 may obtain the maximum axis length Max of the target object along the view angle M, and the minimum axis length Min along the view angle N.

In some embodiments, the target aspect ratio of the target object may be a ratio of the maximum axis length to the minimum axis length. As shown in FIG. 10, the target aspect ratio may be the ratio of the maximum axis length Max of target object along the view angle M to the minimum axis length Min of the target object along the view angle N. The target aspect ratio of the target object may be Max/Min.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 910 and operation 920 may be combined into a single operation. As another example, one or more other optional operations (e.g., a storing operation) may be added elsewhere in the process 900. In the storing operation, the processing device 140 may cause information and/or data (e.g., the image data, the target image, etc.) to be stored in a storage device (e.g., the storage device 150) disclosed elsewhere in the present disclosure. As still another example, in 920, the axis length of the target object may be determined according to an equation $L=|D_2-D_1|\times DetSize \times SID/SDD$, where like symbols denote like parameters as described elsewhere in the present disclosure.

Figures 11, 12:
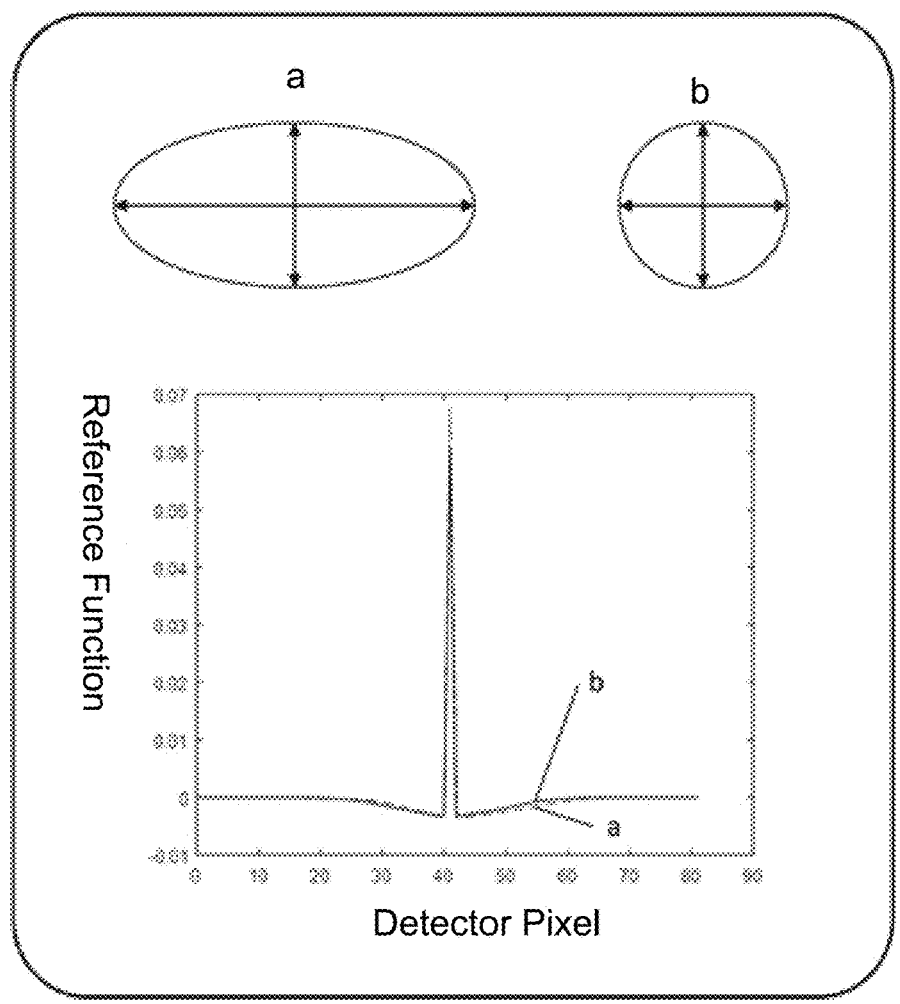
FIG. 11 is a flowchart illustrating an exemplary process for determining a correction function according to some embodiments of the present disclosure.
FIG. 12 is a schematic diagram illustrating reference convolution kernels corresponding to different reference aspect ratios according to some embodiments of the present disclosure.

FIG. 11 is a flowchart illustrating an exemplary process 1100 for determining a correction function according to some embodiments of the present disclosure. In some embodiments, the process 1100 may be implemented as a set of instructions (e.g., an application) stored in the storage device 150 or the storage device 220. The processing device 140 and/or the processor 210 may execute the set of instructions, and when executing the instructions, the processing device 140 and/or the processor 210 may be configured to perform the process 1100. The operations of the illustrated process presented below are intended to be illustrative. In some embodiments, the process 900 may be accomplished with one or more additional operations not described and/or without one or more of the operations discussed. Additionally, the order of the operations of the process 1100 illustrated in FIG. 11 and described below is not intended to be limiting.

In 1110, the processing device 140 (e.g., the processor 210, the correction function determination module 340) may obtain a reference set. In some embodiments, the reference set may include a plurality of reference pairs. In some embodiments, each reference pair of the plurality of reference pairs may include a reference aspect ratio and a reference function with respect to the reference aspect ratio.

In some embodiments, the processing device 140 may obtain a plurality of reference aspect ratios. For example, the processing device 140 may obtain a plurality of reference aspect ratios corresponding to different reference objects based on a statistical analysis. In some embodiments, the reference object may include any human body part (e.g., the heart, the liver, a lung, the stomach, a kidney, the head, a hand, an arm, a foot, a shank, a thigh, the abdomen, the chest, the cervical spine, etc.) of a human. In some embodiments, the processing device 140 may statistically analyze the aspect ratios of various human body parts of different sample human subjects in different regions, at different ages, of different genders, of different heights and/or weights, and having any other different characters. The processing device 140 may determine the plurality of reference aspect ratios based on a statistical result. For example, the reference aspect ratios may include a statistical average value of the aspect ratios of a human body part of human in different regions, at different ages, of different genders, of different heights and/or weights, etc.

In some embodiments, for each reference aspect ratio of the plurality of reference aspect ratios, the processing device 140 may obtain a focus signal distribution and a defocus signal distribution with respect to the reference aspect ratio. In some embodiments, reference objects that have various reference aspect ratios may be provided. In some embodiments, the shape of a reference object may be the same as or similar to the corresponding human body part. For example, the shape of a reference object may include an ellipse, a rectangle, a circle, or the like, or any combination thereof. In some embodiments, a material of the reference object may include water, a polymethylmethacrylate (PMMA), nylon, or the like, or any combination thereof.

In some embodiments, the processing device 140 may cause a reference object to be scanned using the imaging device including a radiation source (or an X-ray source). In some embodiments, the radiation source may emit a focused signal passing through a focus of the radiation source and a defocused signal scatting from the focused signal. In some embodiments, the processing device 140 may obtain the focus signal distribution and the defocus signal distribution from a detector of the imaging device. In some embodiments, the focus signal distribution may be obtained from a detecting area corresponding to the focused signal. In some embodiments, the focus signal distribution may be a signal distribution of a focused signal after a focused X-ray passes through the reference object. In some embodiments, the defocus signal distribution may be obtained from a detecting area corresponding to a defocused signal. In some embodiments, the defocus signal distribution may be a signal distribution of rays scattered by the focus of the radiation source (e.g., an X-ray tube) after the defocused X-ray passes through the reference object. Since the defocused signal as used herein refers to a signal distribution of the rays scattered by the focus impinging on the detector after having traversed a boundary of the reference object, the defocused signal may generally be distributed at or around the boundary of the image. As shown in FIG. 8, the focus signal distribution may be obtained from a detecting area 2 of the detector, and the defocus signal distribution may be obtained from a detecting area 1 and/or a detecting area 3 of the detector.

In some embodiments, the processing device 140 may simulate scanning the reference object using a computer. For example, the processing device 140 may simulate the signal distributions of the focused signal and the defocused signal passing through the reference object using the computer. A simulation of a signal distribution of the focused signal generated by a focused X-ray that has passed through the reference object may provide a focus signal distribution. A simulation of a signal distribution of the defocused signal generated by a focused X-ray that has passed through the reference object may provide a defocus signal distribution.

In some embodiments, the processing device 140 may obtain a reference function corresponding to the reference aspect ratio of the reference object based on focus signal distribution and the defocus signal distribution. In some embodiments, the focus signal distribution and the defocus signal distribution may be obtained using the imaging device 110 to scan a reference object, or may according to the stimulated scanning using the computer. In some embodiments, the reference function may be a correction algorithm, a correction coefficient, a weight function, or the like, or any combination thereof. For example, the reference function may be a reference convolution kernel. In some embodiments, the energy of an signal that should be detected on a pixel (corresponding to the focus of the radiation source) of the detector may be disperse to an adjacent pixel due to the defocus, the reference convolution kernel of an $i^{th}$ pixel of the detector may be determined according to Equation (6):

$$I_p * K = I_{off},  \quad (6)$$

where $I_p$ denotes the focus signal distribution that is generated by the radiation source by scanning the reference object corresponding to the reference aspect ratio, $I_{off}$ denotes the defocus signal distribution that is generated by the radiation source via scanning the reference object corresponding to the reference aspect ratio, and K denotes a reference convolution kernel corresponding to the reference aspect ratio.

The reference set may be generated by repeating the process described above for multiple reference objects of various reference aspect ratios. In some embodiments, the reference set may be generated by a processing device other than 140 of the imaging system 100. For instance, the reference set may have been generated by the manufacturer of the imaging system 100 or a portion thereof, or a third party. The reference set may be stored on a storage device accessible by the processing device 140.

In some embodiments, each detector may have a reference set including reference functions corresponding to reference aspect ratios. Different detectors may have different reference sets. For a same reference aspect ratio, different detectors may have different reference functions corresponding to the same reference aspect ratio. In some embodiments, the processing device 140 may obtain a plurality of reference functions of each detector with respect to different reference objects corresponding to different reference aspect ratios, and store the plurality of reference functions into a storage device (e.g., the storage device 150, the storage device 220). The processing device 140 may access the storage device to look up a reference function corresponding to a reference aspect ratio (or a reference object of the reference aspect ratio) of a corresponding detector.

FIG. 12 is a diagram illustrating exemplary reference function corresponding to different reference aspect ratios according to some embodiments of the present disclosure. As shown in FIG. 12, for different reference objects corresponding different reference aspect ratios, each detector pixel may correspond to a reference function value (e.g., a reference convolution kernel). A reference object a with a first reference aspect ratio and a reference object b with a second reference aspect ratio are shown on top-left and top-right of FIG. 12, respectively. FIG. 12 shows the reference functions (e.g., the reference convolution kernels) of the reference object a and the reference object b under each detector pixel. The dotted line denotes a reference function (e.g., a reference convolution kernel) of the reference object a with the first reference aspect ratio, and the solid line denotes a reference function (e.g., a reference convolution kernel) of the reference object b with the second reference aspect ratio. As shown in FIG. 12, the horizontal axis denotes the locations of detector pixels (the pixels of the detector), and the vertical axis denotes the values of a reference function (e.g., a reference convolution kernel) for various detector pixels. A detector pixel may correspond to a detector channel described elsewhere in the present disclosure.

In 1120, the processing device 140 (e.g., processor 210, correction function determination module 340) may determine the correction function based on the reference set and the target aspect ratio.

In some embodiments, the processing device 140 may obtain at least two reference pairs from the reference set according to the target aspect ratio. In some embodiments, a difference between the target aspect ratio and the reference aspect ratio of each of the at least two reference pairs may be less than a difference threshold. In some embodiments, the difference threshold may be a predetermined value. In some embodiments, the target aspect ratio may be a value between the at least two reference aspect ratios. In some embodiments, the target aspect ratio may be greater than or less than one of the at least two reference aspect ratios. In some embodiments, the processing device 140 may obtain the two reference aspect ratios that are closest to the target aspect ratio in the reference set.

In some embodiments, the processing device 140 may obtain reference functions corresponding to the at least two reference aspect ratios. The processing device 140 may obtain the at least two reference functions corresponding to the at least two reference aspect ratios from the reference set determined in 1110.

In some embodiments, the processing device 140 may determine the correction function based on the at least two reference functions. In some embodiments, the processing device 140 may determine the correction function using an interpolation algorithm or an extrapolation algorithm based on the at least two reference functions. For example, the processing device 140 may perform an interpolation algorithm on the at least two reference functions to obtain the correction function. In some embodiments, the interpolation algorithm may include a linear interpolation/extrapolation, a high-order interpolation/extrapolation, a nearest neighbor interpolation/extrapolation, or the like, or any combination thereof. For example, the processing device 140 may determine a correction convolution kernel for by performing a linear interpolation on at least two reference convolution kernels. For example, if the target aspect ratio is R, two reference aspect ratios are R1 and R2, respectively. The two reference aspect ratios R1 and R2 may be closest to the target aspect ratio R among the reference pairs of the reference set. The processing device 140 may obtain two reference convolution kernels $K_1$ and $K_2$ paired with the two reference aspect ratios R1 and R2 by looking up the reference set. The processing device 140 may determine a corrected convolution kernel $K_0$ of the target aspect ratio (the target object with the target aspect ratio) according to Equation (7):

$$K_0 = K_1 + \frac{K_2 - K_1}{R_2 - R_1} \times (R - R_1). \quad (7)$$

In some embodiments, the processing device 140 may obtain the corrected image by correcting the target image using the correction convolution kernel $K_0$.

In some embodiments, the processing device 140 may obtain a reference pair from the reference set according to the target aspect ratio. In some embodiments, a difference between the target aspect ratio and the reference aspect ratio of the reference pair may be less than a difference threshold. For example, the target aspect ratio and the reference aspect ratio may be the same. The processing device 140 may designate a reference function paired with the reference aspect ratio in the reference pair as the correction function.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 1110 may be divided into one or more operations. As another example, one or more other optional operations (e.g., a storing operation) may be added elsewhere in the process 1100. In the storing operation, the processing device 140 may cause information and/or data (e.g., the image data, the target image, etc.) to be stored in a storage device (e.g., the storage device 150) disclosed elsewhere in the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python, or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. The latter scenario, the remote computer may be connected to the user's computer through any type of network, including a local area network (LAN) or a wide area network (WAN), or the connection may be made to an external computer (e.g., through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for correcting an image, comprising:
    at least one storage device including a set of instructions for correcting an image; and
    at least one processor in communication with the at least one storage device, wherein when executing the set of instructions, the at least one processor is directed to cause the system to perform operations including:
        obtaining image data of a target object;
        determining a target image based on the image data;
        determining a target aspect ratio of the target object in the target image;
        determining a correction function for correcting artifacts in the target image based on the target aspect ratio; and
        obtaining a corrected image of the target image by correcting the target image based on the correction function.

2. The system of claim 1, wherein the determining a target aspect ratio of the target object in the target image includes:
    obtaining a sinogram of the target object based on the image data;
    determining a plurality of axis lengths of the target object under a plurality of view angles based on the sinogram and a threshold; and
    determining the target aspect ratio of the target object based on the plurality of axis lengths, wherein the target aspect ratio is a ratio of a maximum axis length to a minimum axis length among the plurality of axis lengths.

3. The system of claim 2, wherein the determining a plurality of axis lengths of the target object under a plurality of view angles based on the sinogram and the threshold includes:
    for each view angle of the plurality of view angles,
        obtaining a chord under the view angle based on the sinogram;
        identifying, on the chord, a first pixel having a first value that exceeds the threshold;
        identifying, on the chord, a second pixel having a second value that exceeds the threshold; and
        determining an axis length of the target object under the view angle based on the first pixel, the second pixel, and geometric parameters of a detector that captures the image data.

4. The system of claim 3, wherein the identifying, on the chord, a first pixel having a first value that exceeds the threshold includes:
    performing a first scan, from a first end of the chord, of the chord along a first direction; and
    identifying the first pixel that is the first one, during the first scan, whose value exceeds the threshold.

5. The system of claim 4, wherein the identifying, on the chord, a second pixel having a first value that exceeds the threshold includes:
    performing a second scan, from a second end of the chord, the chord along a second direction that is opposite to the first direction; and
    identifying the second pixel that is the first one, during the second scan, whose value exceeds the threshold.

6. The system of claim 1, wherein the determining a corrections function for correcting artifacts in the target image based on the target aspect ratio includes:
    obtaining a reference set including a plurality of reference pairs, each reference pair of the plurality of reference pairs corresponding to a reference aspect ratio and a reference function with respect to the reference aspect ratio; and
    determining the correction function based on the reference set and the target aspect ratio.

7. The system of claim 6, wherein the reference function is a reference convolution kernel, and the correction function is a correction convolution kernel.

8. The system of claim 6, wherein the obtaining a reference set includes:
    obtaining a plurality of reference aspect ratios;
    for each reference aspect ratio of the plurality of reference aspect ratios, obtaining a focus signal distribution and a defocus signal distribution with respect to the reference aspect ratio; and determining the reference function with respect to the reference aspect ratio based on the focus signal distribution and the defocus signal distribution.

9. The system of claim 8, wherein the obtaining a focus signal distribution and a defocus signal distribution with respect to the reference aspect ratio includes:

providing a reference object that has the reference aspect ratio;

scanning the reference object using a radiation source, wherein the radiation source emits a focused signal passing through a focus of the radiation source and a defocused signal scatting from the focused signal; and obtaining the focus signal distribution and the defocus signal distribution from a detector that captures the target image, wherein the focus signal distribution is obtained from a detecting area corresponding to the focused signal, and the defocus signal distribution is obtained from a detecting area corresponding to the defocused signal.

10. The system of claim 9, wherein the reference object includes at least one of a water phantom, a polymethylmethacrylate (PMMA) phantom, or a nylon phantom.

11. The system of claim 6, wherein the determining the correction function based on the reference set and the target aspect ratio includes:

obtaining at least two reference aspect ratios from the reference set based on the target aspect ratio;

obtaining at least two reference functions corresponding to the at least two reference aspect ratios; and determining the correction function based on the at least two reference functions.

12. The system of claim 11, wherein a difference between the target aspect ratio and at least one of the at least two reference aspect ratios is less than a difference threshold.

13. The system of claim 11, wherein the correction function is determined based on the at least two reference functions using an interpolation algorithm or an extrapolation algorithm.

14. The system of claim 13, wherein the interpolation algorithm includes at least one of a linear interpolation, a high-order interpolation, or a nearest neighbor interpolation.

15. The system of claim 1, wherein the obtaining a corrected image of the target image by correcting the target image based on the correction function includes:

determining an original intensity distribution function based on the target image;

determining an error function based on the original intensity distribution function and the correction function;

determining a corrected intensity distribution based on the original intensity distribution and the error function; and obtaining the corrected image by reconstructing the target image based on the corrected intensity distribution.

16. A method for correcting an image, comprising:
obtaining image data of a target object;

determining a target image based on the image data;

determining a target aspect ratio of the target object in the target image;

determining a correction function for correcting artifacts in the target image based on the target aspect ratio; and obtaining a corrected image of the target image by correcting the target image based on the correction function.

17. The method of claim 16, wherein the determining a target aspect ratio of the target object in the target image includes:

obtaining a sinogram of the target object based on the image data;

determining a plurality of axis lengths of the target object under a plurality of view angles based on the sinogram and a threshold; and determining the target aspect ratio of the target object based on the plurality of axis lengths, wherein the target aspect ratio is a ratio between a maximum axis length and a minimum axis length among the plurality of axis lengths.

18. The method of claim 16, wherein the determining a corrections function for correcting artifacts in the target image based on the target aspect ratio includes:

obtaining a reference set including a plurality of reference pairs, each reference pair of the plurality of reference pairs corresponding to a reference aspect ratio and a reference function with respect to the reference aspect ratio; and determining the correction function based on the reference set and the target aspect ratio.

19. The method of claim 16, wherein the obtaining a corrected image of the target image by correcting the target image based on the correction function includes:

determining an original intensity distribution function based on the target image;

determining an error function based on the original intensity distribution function and the correction function;

determining a corrected intensity distribution based on the original intensity distribution and the error function; and obtaining the corrected image by reconstructing the target image based on the corrected intensity distribution.

20. A non-transitory readable medium, comprising at least one set of instructions for correcting an image, wherein when executed by at least one processor of an electrical device, the at least one set of instructions directs the at least one processor to perform a method, the method comprising:

obtaining image data of a target object;

determining a target image based on the image data;

determining a target aspect ratio of the target object in the target image;

determining a correction function for correcting artifacts in the target image based on the target aspect ratio; and obtaining a corrected image of the target image by correcting the target image based on the correction function.

* * * * *